US006789428B2

(12) United States Patent
Nishimura et al.

(10) Patent No.: US 6,789,428 B2
(45) Date of Patent: Sep. 14, 2004

(54) METHOD AND APPARATUS FOR EVALUATING DAMAGE OF METAL MATERIAL

(75) Inventors: Nobuhiko Nishimura, Nagasaki (JP); Keiichi Iwamoto, Nagasaki (JP); Masafumi Yamauchi, Nagasaki (JP); Takumi Tokiyoshi, Nagasaki (JP); Takao Hashimoto, Nagasaki (JP); Masaaki Fujita, Tokyo (JP); Toshihiko Imamoto, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/445,352

(22) Filed: May 27, 2003

(65) Prior Publication Data

US 2003/0200810 A1 Oct. 30, 2003

Related U.S. Application Data (62) Division of application No. 09/716,383, filed on Nov. 21, 2000, now Pat. No. 6,606,910.

(30) Foreign Application Priority Data

Nov. 29, 1999 (JP) .......................................... 11-338672

(51) Int. Cl.[7] ................................................. G01N 9/24
(52) U.S. Cl. ............................ 73/627; 73/599; 73/602; 73/799
(58) Field of Search .......................... 73/627, 599, 602, 73/799, 783, 787, 760, 600, 822

(56) References Cited

U.S. PATENT DOCUMENTS

| 4,492,118 A | * | 1/1985 | Bathmann et al. ............. 73/612 |
| 4,567,774 A | | 2/1986 | Manahan et al. .............. 73/826 |
| 4,570,487 A | * | 2/1986 | Gruber ......................... 73/624 |
| 4,685,335 A | * | 8/1987 | Sato et al. ..................... 73/660 |
| 4,719,583 A | * | 1/1988 | Takafuji et al. ............... 702/30 |
| 4,768,383 A | * | 9/1988 | Koyama et al. .............. 73/787 |
| 5,677,490 A | * | 10/1997 | Gunther et al. ............... 73/622 |
| 5,907,098 A | * | 5/1999 | Tsuboi et al. ................. 73/579 |
| 6,138,514 A | * | 10/2000 | Iwamoto et al. .............. 73/622 |
| 6,382,028 B1 | * | 5/2002 | Wooh et al. .................. 73/602 |
| 6,439,054 B1 | * | 8/2002 | Gore et al. .................... 73/620 |
| 6,606,910 B1 | * | 8/2003 | Nishimura et al. ........... 73/627 |

FOREIGN PATENT DOCUMENTS

| JP | 6-11500 | 1/1994 |
| JP | 8-201359 | 8/1996 |
| JP | 11-316215 | 11/1999 |

\* cited by examiner

*Primary Examiner*—Hezron Williams
*Assistant Examiner*—Jacques M. Saint-Surin
(74) *Attorney, Agent, or Firm*—Oblon, Spivak, McClelland, Maier & Neustadt, P.C.

(57) ABSTRACT

A damage evaluation method and apparatus of a metal material which is capable of determining whether a flaw in the metal sample is originated by the creep damage or in the manufacturing process, and also capable of estimating a remaining life of the metal component. The damage evaluation method of a metal material by the present invention is a method for evaluating a flaw in the metal sample comprising the steps of mounting onto a metal surface including an internal flaw and on both sides of the flaw a transmitting probe for transmitting an ultrasonic waves and a receiving probe for receiving the ultrasonic waves, transmitting the ultrasonic waves towards the internal flaw and receiving the diffracted wave from the flaw for determining whether or not a flaw is present in the metal, based on the analysis of the distribution of the diffracted waves and an analysis of the sample as to whether voids (creep voids) are present and, if present, the distribution of the voids.

6 Claims, 6 Drawing Sheets

RELATED ART

METHOD AND APPARATUS FOR EVALUATING DAMAGE OF METAL MATERIAL

BACKGROUND OF THE INVENTION

1. Field of the Invention

The present invention relates to a method and apparatus for evaluating damage of metal materials, and particularly relates to an evaluation method of metal materials suitable for evaluating a brittle creep damage generated at the welded portion of low-alloy steels used for high temperature-high pressure resistant metal members such as boilers in thermal power plants.

2. Background Art

Operating hours of power plants have recently been increasing. Such long operating hours, frequent starting and stopping operations, and rapid load fluctuations of power plants cause creep fatigue of power plant facilities and degrade the plant facilities. In order to cope with degradation due to the thermal fatigue of facilities in power plants, an emphasis is placed on a maintenance technology of power plants, considering creep fatigue of metal components.

For example, thick and large diameter pipes made of high temperature-high pressure resistant steel metal materials are subjected to damage such as cracks which originate, in most cases, in the internally in welded portions. However, since the damage such a crack is difficult to detect externally, development of technology for early detection of the damage such as a crack and a monitoring technique of the crack by an accurate measurement of the crack are problems to be solved.

Conventionally, the crack depth from the surface is measured by an edge echo method based on an ultrasonic flaw detection analysis.

However, in order to detect the crack depth using the edge echo method, it is necessary for an operator to determine the crack depth by reading the subtle change of the edge echo, so that the problem arises that the result of the edge echo method is liable to include personal errors. A method called TOFD (Time of Flight Diffraction technique) is used for detecting the internal defects such as cracks and for determining the quantitative values such as the length of the defect.

Figure 11:
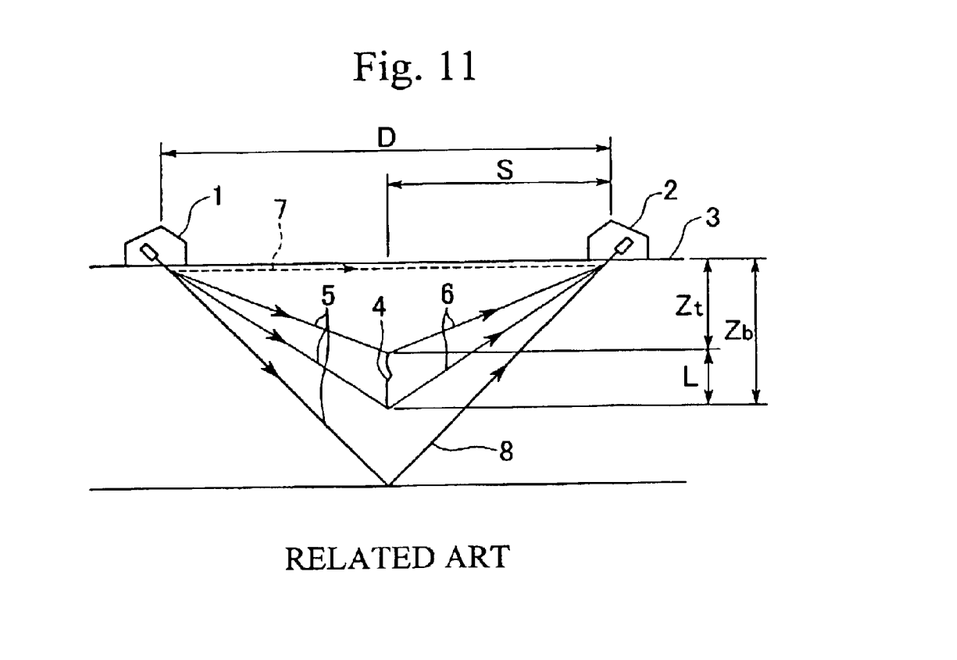
FIG. 11 is a diagram explaining the principles of measurement by the TOFD method.

FIG. 11 is a diagram for explaining the principle of the measurement of the TOFD method. The TOFD system comprises a transmitting probe 1 for transmitting a ultrasonic wave and a receiving probe 2 for receiving the ultrasonic wave. During measurement by the TOFD system, the transmitting probe 1 and the receiving probe 2a are mounted on a metal sample 3 which includes a crack (defect) 4 such that the crack is positioned in the middle of the transmitting and receiving probes and an ultrasonic wave is transmitted obliquely by the transmitting probe 1 towards the crack 4 in the metal plate and the diffracted waves 6 from both of the upper and lower edges of the crack are detected by the receiving probe 2 for measuring the propagation time of the ultrasonic wave. The height of the crack 4 is obtained by measuring the difference between the propagation from the top of the crack and that from the bottom end of the crack by the following equation (1).

$$L = Zb - Zt$$
$$= (tb^2 \cdot V2/4 - S2)^{1/2} - (tt2 \cdot V2/4 - S2)^{1/2}$$

where, L represents the height of the crack; Zb represents the depth of the top of the crack; Zt represents the depth of the crack bottom; D represents the distance between the transmitting and receiving probes; S represents D/2, V represents the velocity of the diffraction wave; tt represents the propagation time of the diffraction wave from the top end of the crack; and tb represents the propagation time of the diffraction wave from the bottom end of the crack.

The above-described TOFD method has the advantage that, since this method measures the diffracted waves from the crack, it is possible to reduce the effect due to slanting of the crack or to reduce the possibility of overlooking directional defects and, as a result, the performance in detecting the defects is improved.

However, when an alloy steel which has been used for 10 to 20 years is examined by the TOFD method, the problem arises that, since it is not possible to determine whether the detected defect is caused as a creep damage due to the aged deterioration or caused in the manufacturing process, the estimation of the remaining service life is difficult.

For example, when a low alloy steel, usually used for thick pipes having large diameters, is examined, it is found that the creep crack growth rate is dependent on the material composition of the low alloy steel, and the impurity content of the metals used for the welded portion. In particular, it is known that the crack growth rate is dependent on the thermal stress for circumferentially welded portion. Furthermore, it was found that the rack develops not at the outside of the pipe but inside of the steel pipe where high stress is applied multiaxiality.

If it is possible to determine whether the crack inside of the pipe is developed by creep damage or generated in the manufacturing process, it becomes possible to estimate the remaining service life of the steel pipe. No study has been reported until now.

SUMMARY OF THE INVENTION

The present invention was made to solve the above problems. It is therefore an object of the present invention to provide a damage evaluation method and the apparatus thereof, which is capable of determining whether an internal crack of a metal material is developed by the creep damage by an aged deterioration or caused in the manufacturing process, and which is capable of evaluating the remaining service life of a metal component.

According to the first aspect of the present invention, a damage evaluation method of a metal material for evaluating a flaw in the metal sample comprises the steps of: mounting onto a meal surface including an internal flaw and on both sides of the internal flaw a transmitting probe for transmitting an ultrasonic wave and a receiving probe for receiving the ultrasonic wave; transmitting the ultrasonic wave towards the internal flaw and receiving the diffracted wave from the internal flaw for determining whether or not a flaw is present in the metal.

In this method, when a flaw is present in a metal sample, an ultrasonic wave transmitted toward the flaw by the transmitting probe is diffracted by the flaw as propagate in the metal sample giving rise to diffracted wave. If the diffracted wave is detected, it is determined that a flaw is present in the metal sample.

According to the second aspect, in the damage evaluation method of a metal material for evaluating a flaw in the metal sample according to the first aspect, it is determined whether the flaw is caused by creep, through metallographic analysis after carrying out the metallographic analysis of the metal surface in which the internal flaw is present.

This method carries out a metallographic analysis for the surface of the metal sample by obtaining a replica of the metal sample and makes it possible to accurately estimate whether the flaw is due to creep by evaluating whether the flaw is present and whether the metal microstructure is degraded.

According to the third aspect, in a damage evaluation method of a metal material for evaluating a flaw in the metal sample, the method comprises the steps of: conducting chemical analysis of a sample taken from the surface of said metal; estimating the creep characteristics of the metal based on the results of the chemical composition analysis; carrying out stress analysis based on the creep characteristics; and determining whether or not said flaw is due to the creep based on the stress analysis.

In this method, a small piece of sample is taken from the surface of said metal sample, the impurity concentrations are determined by the chemical analysis, the creep characteristics of the metal material are estimated, and the stress analysis is carried out based on the creep characteristics. In this stress analysis, since a damage estimate representing the metal sample ductility is obtained, it becomes possible to determine whether the flaw is caused by creep based on the above obtained damage estimate.

According to the fourth aspect, a damage evaluation method of a metal material for evaluating a flaw in the metal sample comprises the steps of: performing a chemical analysis for a sample taken from a surface of said metal; extracting crack propagation data suitable for said metal material from the result of said chemical analysis and a predetermined relationship between impurity concentrations and corresponding crack propagation rate; and determining the remaining service life of the metal sample from the crack propagation rate.

In this method, the impurity concentrations are obtained by the chemical analysis of a small piece of sample obtained from the surface of the metal sample, and crack propagation data suitable for the metal sample is obtained by the impurity concentration and predetermined relationships between the impurity concentrations and the crack propagation rate by the creep. Since the crack propagation data includes the distance of the flaw to the surface of the metal sample, and the crack propagation rate, the time period for the crack reaching the surface of the metal sample can be obtained from the crack propagation behavior shown in the graph representing the relation between the crack height and time. Thus, the remaining service life of the metal sample can be estimated from the crack propagation data.

According to the fifth aspect, a damage evaluation method of a metal material for evaluating a flaw in the metal sample comprises the steps of: carrying out a metallographical analysis for the surface of the metal; estimating the degree to which creep damage has progressed; and extracting the crack propagation data from the thus-estimated degree to which the creep damage has progressed and from the predetermined relationship between the degree to which the creep damage has progressed and the creep crack propagation rate; and determining the remaining life of the metal sample containing the flaw.

In this method, the surface microstructure of the metal sample is analyzed by the replication method, the degree to which the creep damage (creep damage degree) has progressed is estimated based on the metallographical analysis, and the crack propagation data suitable for the metal sample is extracted based on the above estimated creep damage degree, and the predetermined relationship between the creep damage degree and the crack propagation rate. Since the crack propagation data include distance of the flaw to the surface of the metal sample, and the crack propagation rate, the time period for the crack reaching the surface of the metal sample can be obtained as a time when the crack height is equal to the wall thickness. Thus, the remaining service life of the metal sample can be estimated from the crack propagation data.

According to the sixth aspect, a damage evaluation method of a metal material for evaluating a flaw in the metal sample is provided, wherein the damage evaluation method for evaluating a flaw in the metal sample uses the damage evaluation method according to the first aspect, the damage evaluation method according to the second aspect, and the damage evaluation method according to the fifth aspect.

This method makes it possible to determine whether the flaw is caused by the creep damage and to estimate the remaining service life of the metal sample with the flaw.

According to the seventh aspect, a damage evaluation method of a metal material for evaluating a flaw in the metal sample is provided, wherein the damage evaluation method for evaluating a flaw in said metal sample uses the damage evaluation method according to the first aspect, and the damage evaluation method according to the third aspect.

This method makes it possible to determine accurately whether the flaw is caused by the creep.

According to the eighth aspect, a damage evaluation method of a metal material for evaluating a flaw in the metal sample is provided, wherein the damage evaluation method for evaluating a flaw in said metal sample uses the damage evaluation method according to the first aspect, and the damage evaluation method according to the third aspect, and the damage evaluation method according to the fourth aspect.

This method makes it possible to determine whether the flaw is caused by the creep damage and to estimate the remaining service life of the flaw.

According to the ninth aspect, a damage evaluation apparatus of a metal material for evaluating a flaw in the metal sample is provided, wherein the damage evaluation apparatus for evaluating a flaw in the metal material comprises: a creep characteristic estimation device for estimating the creep characteristics of said metal material based on the chemical analysis of the metal sample taken from the surface of said metal sample; a determining device for determining whether or not said flaw is originated by the creep by carrying out the stress analysis based on said creep characteristics of the metal material.

This apparatus makes it possible to determine in a more accurate and prompt manner whether the flaw is caused by creep.

According to the tenth aspect, the damage evaluation apparatus of a metal material for evaluating a flaw in the metal sample comprises: a data extracting device for estimating the crack propagation data suitable for said metal material from the results of the chemical analysis of the surface of said metal sample and from the relationship between predetermined impurity concentration and crack propagation velocities; and a remaining service life estimating device for estimating the remaining service life of the metal material including the flaw.

This apparatus makes it possible to determine in more accurate and prompt manner whether the flaw is caused by the creep.

According to the eleventh aspect, the damage evaluation apparatus of a metal material for evaluating a flaw in the metal sample comprises: a creep damage estimation device for estimating the degree to which the creep damage has progressed based on the results of the metallographical analysis of the surface of said metal sample; a crack propagation data extracting means for extracting the crack propagation data suitable for said metal material from the thus estimated degree to which the creep damage has progressed and from the relationship between a predetermined degree to which the creep damage has progressed and the crack propagation rate; and a remaining service life estimation device for estimating the remaining service life of said metal material.

This apparatus makes it possible to estimate in more accurate and prompt manner the remaining service life of the metal sample.

DETAILED DESCRIPTION OF THE INVENTION

The damage evaluation method of metal components according to the present invention and the damage evaluation apparatus according to the embodiments of the present invention are described with reference to the attached drawings.

[First Embodiment]

Figure 1:
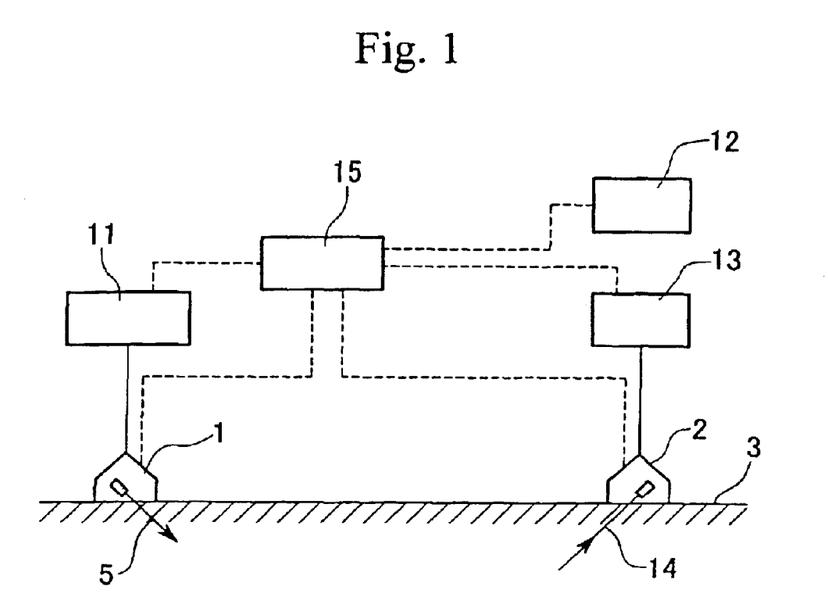
FIG. 1 is a block diagram showing a damage evaluation apparatus according to the first embodiment of the present invention.

FIG. 1 is a block diagram showing a damage evaluation apparatus according to the first embodiment of the present invention. In FIG. 1, reference numeral 11 denotes an oscillator for making the transmitting probe 1 to transmit ultrasonic waves. Numeral 12 denotes a creep characteristic estimation portion (a creep characteristic estimation device) for estimating the creep characteristic of the metal materials based on the chemical analysis of a sample taken from the surface of the metal material 3, numeral 13 is a determination portion (determination device) for determining whether the damage is caused by the creep based on the result of the stress analysis, which is carried out based on the creep characteristics and based on the distribution of the diffraction waves which are received from the damage detected by the receiving probe in the metal sample 3, and numeral 15 is a control portion for controlling the operation of the transmitting probe 1, the receiving probe 2, the oscillator 11, the creep characteristic estimation portion 11, and the determination portion 13.

Figure 2A:
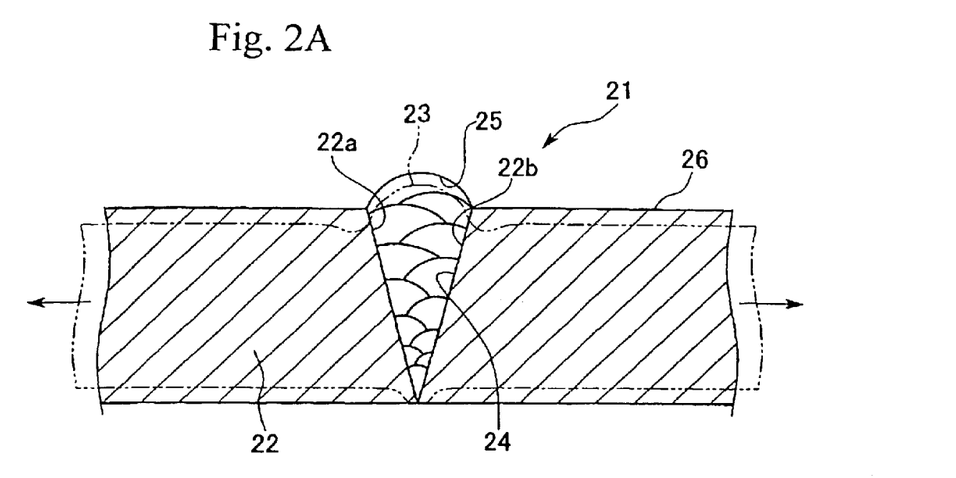
FIG. 2A is a cross-sectional views of a welded portion of a high temperature pipe according to the first embodiment of the present invention, an FIG. 2B shows a relationship between the creep damage degree of the weld metal and an impurity concentration.

FIG. 2A is a cross-sectional view of a welded portion of a high temperature pipe used as one example of the metal sample 3. In FIG. 2A, reference numeral 21 is a high temperature pipe made of a low alloy steel, and the low alloy steel plates 22 and 26 are processed by folding into pipes and both end surfaces 22a and 26b along the longitudinal directions are welded using a weld metal 23. A flaw 24 is developed in the weld metal 23.

This weld metal has a composition of, for example, 2.25% Cr—1% Mo—0.12% C and a balance of Fe, wherein P (phosphorus), As (arsenic), Sn (tin), and Sb (antimony) are important impurities which affect the crack growth rate due to the creep damage.

Figure 2B:
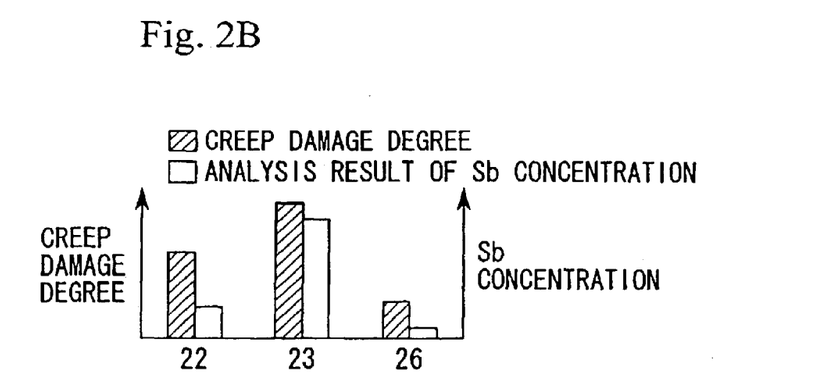

As shown in FIG. 2B, the creep damage degree (consumed life fraction) of the weld metal 23 is higher than those of the surrounding steel plates 22 and 26, and it was observed that the antimony concentration obtained by the chemical analysis of these metal materials is a dominating factor in determining the creep damage degrees of these steel materials.

Figure 3:
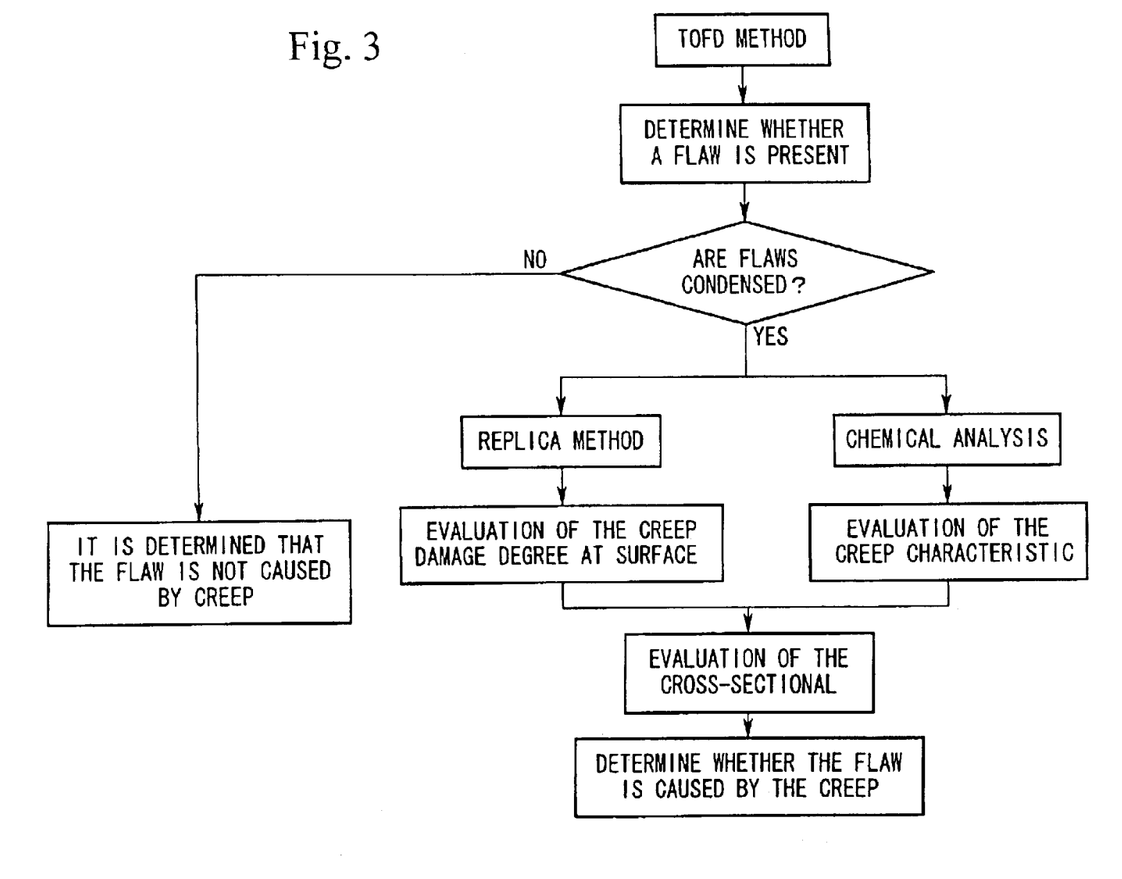
FIG. 3 is a flow-chart showing the damage evaluation method of a metal sample according to the first embodiment of the present invention.

A damage evaluation method of the metal materials using an example of the high temperature steel pipe according to the present embodiment is described below with reference to FIG. 3.

1. Ultrasonic Examination by the TOFD Method and Classification of Flaws.

(1) Ultrasonic Flaw Detection by the TOFD Method

A transmitting probe 1 and a receiving probe 2 are placed on both sides of the welded portion, the probes being equal distances apart from a flaw 24 in the welded portion. Ultrasonic waves 5 are transmitted towards the flaw 24 from the transmitting probe 1 and the diffracted waves 14 from the flaw 24 is detected for determining whether the flaw 24 is present in the high temperature steel pipe. When the flaw is detected, the position, height, and length of the flaw 24 are obtained. The position of the flaw 24 is identified by moving both the transmitting probe 1 and the receiving probe 2 along the welded line.

(2) Classification of the Detected Flaws

The detected flaws are classified into one of three types of flaws.

The flaws detected by the TODF method can be classified into one of the three following types.

"A" Type Flaw (Dense Flaws)

A plurality of small flaws estimated to be densely located. For example, two flaws estimated to have the same length are located closely and the interval between the two flaws is shorter than the length of the longer flaw.

"B" Type Flaw
Flaws estimated to extend in two-dimensions.
"C" Type Flaw
Flaws estimated to extend in three-dimensions by, for example, involution of a slug.

2. Determination by the Replication Method (1) Sampling by Replication

A replica of the surface of the high temperature steel pipe 21 is obtained as a replica 25 by using the replication method.

For example, the surface of the steel pipe 21 is finished into a mirror surface after rough and fine polishing, and a plastic film for replication is pressingly adhered to the mirror finished surface after being subjected to etching for copying the surface microstructure of the pipe on the replica film.

(2) Observation and Determination of the Replica Surface

The replica surface is observed with an optical microscope for examining whether there are voids (creep voids) due to the creep damage. In this step, it is roughly determined whether the flaw 24 is caused by creep.

Subsequently, the surface is precisely examined under the scanning electron microscope (SEM) to determine whether the creep voids are present or not, and when creep voids are found, the distribution of the creep voids are precisely examined. For example, the number of the creep voids is measured and the density of the creep voids is obtained for estimating the creep damage degree (consumed life fraction) from the life evaluation diagram (graph showing the relationship between the creep voids density and the creep damage degree).

As described above, when the creep damage is observed, it is determined that creep causes the flaw 24. In contrast, when the damage by the creep is not observed in the replica 25, it is determined that the flaw 25 is not caused by the creep damage (caused in the manufacturing process).

3. Determination by the Chemical Analysis of the Metal Composition (1) Impurity Analysis A surface oxide layer on the sample region of the weld metal 23 is removed by grinding and the thus finished metal surface is ground for sampling metal chips. Subsequently, the concentrations of P, As, Sn, and Sb in the chips are analyzed. The analysis has been performed by the atomic absorption analysis for P and by the hydride-generated ICP emission spectral analysis for As, Sn, and Sb.

(2) Creep Characteristic Evaluation

Subsequently, based on the impurity analysis, the creep embrittlement factor (CEF) is obtained by the following equation.

$$CEF = P(\text{wt \%}) + 2.4As\,(\text{wt \%}) + 3.6Sn\,(\text{wt \%}) + 8.2Sb\,(\text{wt \%}) \quad (2)$$

The creep damage degree (life consumption rate) is estimated from the CEF value and the result of the pipe stress calculation executed separately and it is determined from the creep damage degree whether or not the flaw 24 is generated by the creep.

4. Cross Sectional Flaw Distribution Evaluation

Figure 4:
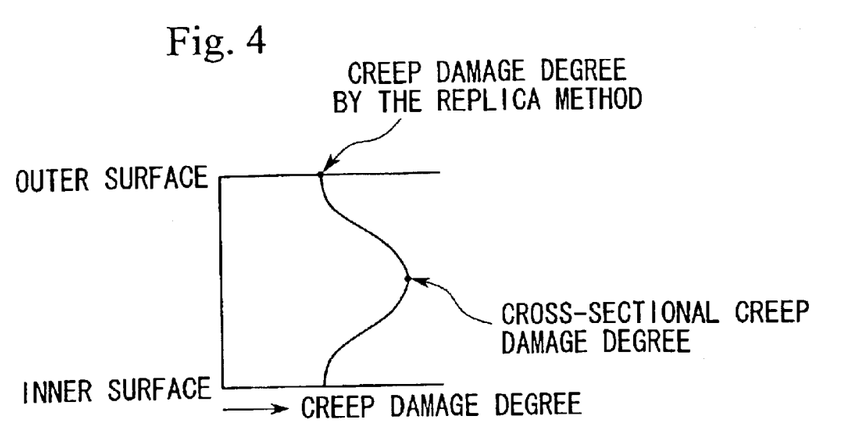
FIG. 4 is a diagram showing a distribution of the creep damage in the welded portion of a high temperature pipe according to the first embodiment of the present invention.

Based on the creep damage degree obtained by the replica observation and the impurity analysis, the cross-sectional distribution of the creep damage degree of the weld metal is obtained, and based on the cross-sectional distribution of the creep damage degree, it is determined whether the flaw is caused by creep.

It is noted that the above-described creep damage degree can be evaluated by stress analysis in addition to the replication method.

The stress analysis is carried out by the use of the finite element method in which a piping system having a weld joint is converted into an equivalent beam model with the same rigidity, and the supporting portion and the fixing portion are provided with the above model as if in the practical pipe, and the temperature of the model is raised to the same temperature to which the practical component is exposed. The pipe is expected to expand corresponding to the temperature. However, stress is generated in the pipe because deformation due to the thermal expansion is restricted by the supporting portion and the fixing portion.

Since this stress is macro-structural stress generated in the piping system, this stress can be analyzed by applying the stress to the above-described model, in which effects of the base metal, the thermal effect, and the creep characteristic of the weld metal are taken into consideration. In this analysis, the effect of the impurities are taken into consideration as the characteristics of the material used, and the effect of the internal multiple axis restriction is obtained as the result of the analysis. Furthermore, the creep damage distribution in the thickness direction can be obtained from the stress distribution generated in the thickness direction of the joint portion.

As described above, the damage evaluation method according to the present embodiment is capable of more accurately determining whether the flaw 24 generated in the weld metal is caused by creep.

In addition, the damage evaluation apparatus according to the present embodiment is capable of accurately and rapidly determining whether the flaw 24 generated in the welded metal is caused by the creep.

[Second Embodiment]

Figure 5:
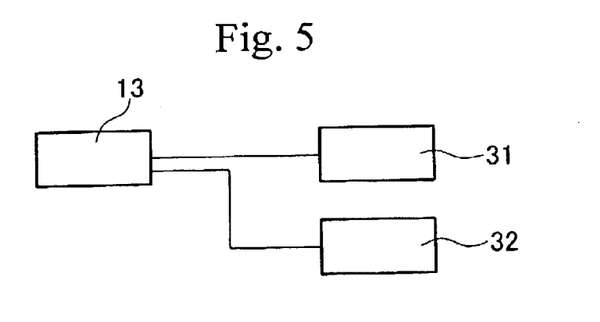
FIG. 5 is a block diagram showing a main potion of the damage evaluation apparatus of metal materials according to the second embodiment of the present invention.

FIG. 5 is a block diagram showing a constitution of the damage evaluation apparatus of metals according to the second embodiment of the present invention. the apparatus according to the second embodiment differs from that according to the first embodiment in that the determining portion 13 comprises a data extracting portion (data extracting device) 31 for extracting the crack propagation data suitable for the particular metal 3 from both of the result of the chemical analysis of the sample obtained from the metal 3 surface and the relationship between the thus obtained chemical composition and the creep crack propagation rate, and a remaining life estimation portion (remaining life estimation device) 32 for estimating the remaining life of the flaw 24 based on the thus obtained crack propagation data.

Next, the damage evaluation method according to the second embodiment will be described in the case of the high temperature pipe 21 shown in FIG. 2.

1. Ultrasonic Flaw Detection by TOFD and Classification of Flaws

The method is the same as the first embodiment and thus the explanation is omitted.

2. Creep Characteristic Evaluation

Similar to the first embodiment, concentrations of impurities such as P, As, Sn, and Sb are obtained by chemical analysis and a creep embrittlement factor (CEF) is obtained based on the results of the impurity concentration.

Subsequently, the accumulated creep damage is estimated by the replication method or the stress analysis, similar to the first embodiment.

Figure 6:
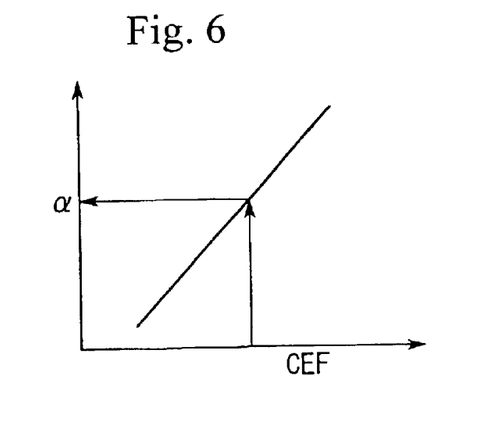
FIG. 6 is a schematic diagram showing the relationship between the creep embrittlement factor (CEF) and the creep crack propagation rate growth factor ($\alpha$) due to the impurity.

Subsequently, the creep crack propagation rate growth factor ($\alpha$) dependent on the impurities is obtained from the thus obtained CEF value. FIG. 6 can be obtained by carrying out the creep crack propagation tests for high temperature steel pipe samples 21 having different impurity concentrations. As a reference, the creep crack propagation rate growth factor ($\alpha$) is set at "1".

Figure 7:
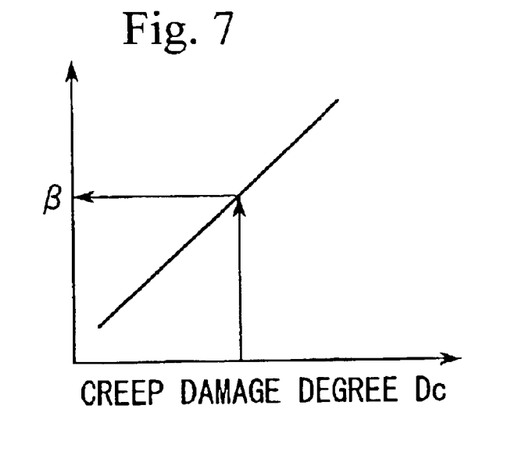
FIG. 7 is a schematic diagram showing the relationship between the creep damage degree (Dc) and the creep crack propagation rate growth factor ($\alpha$) due to the creep.

Furthermore, the creep crack propagation rate growth factor ($\beta$), which depends on the creep damage, is obtained from FIG. 7. FIG. 7 is obtained by carrying out creep crack propagation tests for various high temperature pipe 21 samples having different creep cracks. As a reference, the creep crack propagation rate growth factor (β) for low impurity high temperature steel is set at "1" (in FIG. 7, DC represents the creep damage).

Subsequently, the creep crack propagation rate (da/dt) is obtained taking the impurity concentration and the degree of the creep damage into consideration by using the following formula (3).

$$da/dt = a \cdot \beta \cdot A \cdot (C^*)B \tag{3}$$

where, A and B are material constants, and $C^*$ is a fracture mechanics parameter dependent on the stress and the creep characteristics of the material.

Subsequently, the creep crack propagation life is obtained from the above equation (3).

Following the steps described above, the remaining service life of the material including the flaw 24 can be obtained by the use of the creep crack propagation rate obtained in the equation (3).

The damage evaluation method of the metal material according to the present embodiment is capable of accurately determining whether the flaw generated in the welded metal is caused due to creep, and is also capable of obtaining the remaining service life of the metal material including the flaw 24.

[Third Embodiment]

Figure 8:
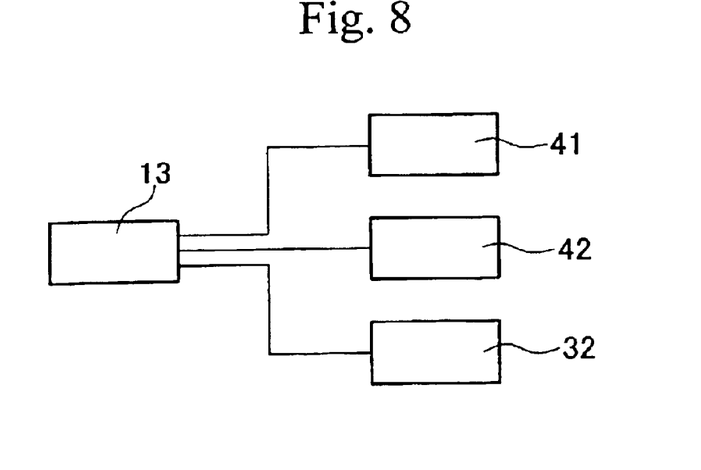
FIG. 8 is a block diagram showing a main potion of the damage evaluation apparatus of metal materials according to the third embodiment of the present invention.

FIG. 8 is a block diagram showing the main portion of the damage evaluation apparatus of the metal material according to the third embodiment of the present invention. The apparatus according to the third embodiment differs from that according to the second embodiment in that the apparatus comprises, instead of the data extracting portion, a creep damage estimation portion (creep damage estimation device) 41 for estimating the damage degree based on the metallographical analysis of the sample surface (by the replica method) and a data extracting portion (data extracting portion) 42 for extracting a suitable creep crack propagation data for the sample from the thus obtained creep damage degree, and a relationship between the degree to which creep damage has progressed, obtained in advance, and the creep crack propagation rate.

The damage evaluation data of the metal material according to the third embodiment is described for the case of the high temperature steel metal 21 shown in FIG. 2.

1. Ultrasonic Flaw Detection and Classification of the Flaw

The same method as the first embodiments is used so that the explanation is omitted.

2. Determination by Replication

Similar to the first embodiment, a replica of the high temperature steel pipe is observed and the degree to which creep damage has progressed (the creep damage degree) is estimated.

Figure 9:
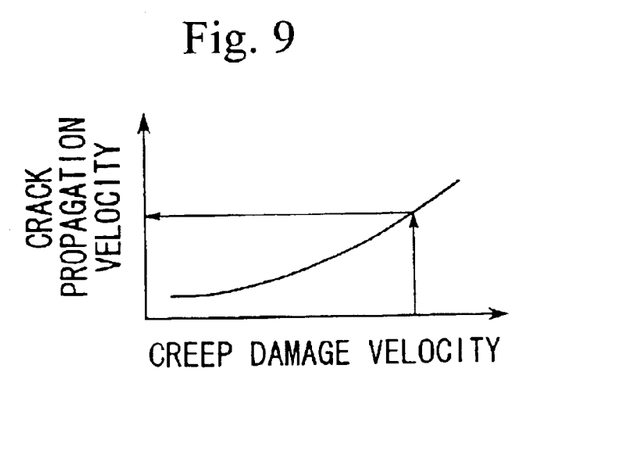
FIG. 9 is a schematic diagram showing the relationship between the creep damage degree (Dc) and the creep crack propagation rate growth factor ($\alpha$) due to the creep.

Subsequently, the crack propagation rate by the creep is obtained from the thus estimated creep damage degree by using FIG. 9.

Figure 10:
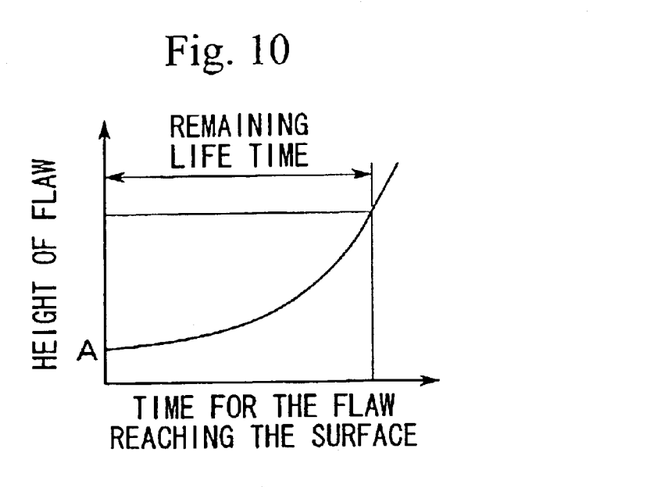
FIG. 10 is a diagram showing the relationship between the time for the crack until arriving at the surface and the height of the crack.

Next, the time period per unit depth until the flaw reaches the surface is obtained by dividing the distance of the flaw to the sample surface by the crack propagation rate, so that the remaining service life of the metal material including the flaw can be obtained from FIG. 10 using the relationship between the time period per unit depth and the depth of the flaw. The point A shown in FIG. 10 is the depth of the measured flaw 24.

The damage evaluation method of a metal material according to the third embodiment makes it possible to accurately determine whether or not the flaw originated in the weld metal is caused by the creep, and to obtain the remaining service life of the metal material including the flaw 24.

As described above, the damage evaluation method and apparatus of the present invention is described using three embodiments with reference to the attached drawings. However, the present invention is not limited to the three embodiments described above and variants thereof can be envisaged without passing beyond the scope of the invention. For example, a variation of the damage evaluation apparatus may be used, which makes use of the reflected wave of an ultrasonic wave. This damage evaluation apparatus comprises a transmitting probe and a receiving probe placed onto a metal plate on both sides of an internal flaw and the presence of the flaw is determined by detecting by the receiving probe reflected ultrasonic waves.

As described above, the damage evaluation apparatus of a metal material according to the first aspect of the present invention is capable of determining whether a flaw generated in the metal is caused by the creep or by other reasons (such as flaws generated in the manufacturing process) by analyzing the distribution of the diffracted wave from the flaw, and is also capable of estimating the remaining service life of the metal material. As a result, the remaining service life of a metal sample used for a long time under high temperature and high stress conditions can be easily estimated within a short test period.

The damage evaluation apparatus according to the second aspect is capable of determining whether the flaw generated in the metal is caused by the creep by the metallographical analysis of the metal surface and also capable of estimating the remaining service life of the metal material. As a result, the remaining service life of a metal sample used for a long time under high temperature and high stress conditions can be easily estimated within a short test period.

The damage evaluation apparatus according to the third aspect is capable of determining whether the flaw generated in the metal is caused by creep by estimating the creep characteristics of the metal sample from chemical analysis of the metal composition and by carrying out the stress analysis based on the thus obtained creep characteristics, and is also capable of estimating the remaining service life of the metal material. As a result, the remaining service life of a metal component used for a long time under high temperature and high stress conditions can be easily estimated within a short test period.

The damage evaluation apparatus according to the fourth aspect is capable of determining whether or not the flaw generated in the metal is caused by the creep by extracting the suitable crack propagation data for the metal sample from the chemical analysis data of the metal surface, and from the relationship between the predetermined element concentration and the creep crack propagation rate, and is also capable of estimating the remaining service life of the metal material from the above crack propagation data. As a result, the remaining service life of a metal component used for a long time under high temperature and high stress conditions can be easily estimated within a short test period.

The damage evaluation apparatus according to the fifth aspect is capable of determining whether or not the flaw generated in the metal is caused by the creep by estimating the creep damage degree from the metallographical analysis of the metal surface, and the crack propagation rate data suitable for the metal sample is extracted from the relationship between the thus estimated degree of creep damage and the creep crack propagation rate data corresponding to that degree of creep damage, and is also capable of estimating the remaining service life of the metal material from the above extracted data. As a result, the remaining service life of a metal component used for a long time under high temperature and high stress conditions can be estimated easily within a short test period.

The damage evaluation apparatus according to the sixth or the eighth aspect is capable of determining whether or not the flaw generated in the metal is caused by the creep damage and the remaining service life of the metal sample can be accurately estimated. As a result, the remaining service life of a metal component used for a long time under high temperature and high stress conditions can be easily estimated within a short test period.

The damage evaluation apparatus according to the seventh aspect is capable of determining whether or not the flaw generated in the metal is caused by the creep damage and the remaining service life of the metal sample can be accurately estimated. As a result, the remaining service life of a metal component used for a long time under high temperature and high stress conditions can be estimated easily within a short test period.

The damage evaluation apparatus according to the ninth or the tenth aspect is capable of determining whether or not the flaw originated in the metal is caused by the creep damage by the use of the result of the chemical analysis of the metal surface and the remaining service life of the metal sample can be accurately estimated. As a result, the remaining service life of a metal component used for a long time under high temperature and high stress conditions can be estimated easily within a short test period.

The damage evaluation apparatus according to the eleventh aspect is capable of determining whether or not the flaw originated in the metal is caused by the creep damage by the use of the result of the metallographical analysis and the remaining service life of the metal sample can be accurately estimated. As a result, the remaining service life of a metal component used for a long time under high temperature and high stress conditions can be easily estimated within a short test period.

What is claimed is:

1. A damage evaluation method of a metal material for evaluating a flaw in a metal sample of the metal material, comprising the steps of:

mounting onto a surface of the metal sample which internally includes the flaw and on both sides of the flaw a transmitting probe and a receiving probe;

transmitting an ultrasonic wave towards the internal flaw and receiving a diffracted wave from the internal flaw to determine that the flaw is present in the metal sample; and evaluating a property of the metal material to determine whether the flaw is caused by creep.

2. A damage evaluation method of a metal material for evaluating a flaw in a metal sample of the metal material, comprising the steps of:

mounting onto a surface of the metal sample which internally includes the flaw and on both sides of the flaw a transmitting probe for transmitting ultrasonic waves and a receiving probe for receiving the ultrasonic waves; and transmitting the ultrasonic waves towards the internal flaw and receiving a diffracted wave from the internal flaw for determining whether the flaw is present in the metal sample, wherein it is determined whether the flaw is caused by creep by a result of a metallographical analysis after carrying out a metallographical examination of the surface of the metal sample in which the internal flaw is present.

3. A damage evaluation method of a metal material for evaluating an internal flaw in a metal sample of the metal material, comprising the steps of:

conducting chemical analysis of a test sample taken from a surface of said metal sample, estimating creep characteristics of the metal sample based on a result of the chemical analysis, carrying out stress analysis based on the creep characteristics, determining whether said internal flaw is generated due to creep based on a stress analysis, and estimating a time until the internal flaw reaches the surface of the metal sample.

4. A damage evaluation method of a metal material for evaluating a flaw in a metal sample of the metal material, comprising the steps of;

conducting a chemical analysis of a test sample taken from a surface of said metal sample;

extracting crack propagation data suitable for said metal material from a result of said chemical analysis and a predetermined relationship between an elemental concentration and a crack propagation rate of the metal material; and determining the remaining service life of the metal material including said flaw.

5. A damage evaluation apparatus of a metal material for evaluating an internal flaw in a metal sample of the metal material, comprising:

a creep characteristic estimation device configured to estimate a creep characteristics of said metal material based on a chemical analysis of a test sample taken from a surface of said metal sample;

a determining device configured to determine whether or not said flaw is originated by creep by carrying out a stress analysis based on a creep characteristics of the metal material; and an estimating device configured to estimate a time until the internal flaw reaches the surface of the metal sample.

6. A damage evaluation apparatus of a metal material for evaluating a flaw in a metal sample of the metal material, comprising:

a data extracting device for estimating a crack propagation data suitable for said metal material from a result of a chemical analysis of a surface of said metal sample and from a predetermined relationship between an elemental concentration and a crack propagation rate of the metal material; and a remaining service life estimating device for estimating a remaining life of the metal material including said flaw.

* * * * *